(12) United States Patent
Candau

(10) Patent No.: US 6,509,008 B1
(45) Date of Patent: Jan. 21, 2003

(54) SOLUBILIZATION OF 1,3,5-TRIAZINE DERIVATIVES WITH N-ACYL AMINO ACID ESTERS

(75) Inventor: Didier Candau, Bievres (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 10/178,339

(22) Filed: Jun. 25, 2002

(30) Foreign Application Priority Data

Jun. 26, 2001 (FR) .............................. 01 08426

(51) Int. Cl.$^7$ .......................... A61K 7/42; A61K 7/44; A61K 7/00; A61K 31/53

(52) U.S. Cl. .......................... 424/59; 424/60; 424/400; 424/401; 514/241

(58) Field of Search .......................... 424/59, 60, 400, 424/401; 514/241

(56) References Cited

U.S. PATENT DOCUMENTS

| | | |
|---|---|---|
| 2,463,264 A | 3/1949 | Graenacher et al. |
| 4,247,411 A | 1/1981 | Vanlerberghe et al. ...... 252/316 |
| 4,617,390 A | 10/1986 | Hoppe et al. ............... 544/197 |
| 5,166,355 A | 11/1992 | Leistner et al. ............. 548/260 |
| 5,233,040 A | 8/1993 | Raspanti ..................... 544/197 |
| 5,236,698 A | 8/1993 | Richard et al. ............... 424/47 |
| 5,237,071 A | 8/1993 | Leistner et al. ............. 548/260 |
| 5,252,323 A | 10/1993 | Richard et al. ............... 424/59 |
| 5,346,691 A | 9/1994 | Raspanti ..................... 424/59 |
| 5,585,091 A | 12/1996 | Pelzer et al. ................. 424/60 |
| 5,772,987 A | 6/1998 | Hansenne et al. ............ 424/59 |
| 5,801,244 A | 9/1998 | Raspanti ..................... 544/197 |
| 5,849,909 A | 12/1998 | Richard et al. ............. 544/197 |
| 5,976,512 A | 11/1999 | Huber ......................... 424/59 |
| 5,980,872 A | 11/1999 | Luther et al. ................. 424/59 |
| 6,093,385 A | 7/2000 | Habeck et al. ................ 424/59 |
| 6,159,455 A | 12/2000 | Habeck et al. ................ 424/59 |
| 6,235,271 B1 | 5/2001 | Luther et al. ................. 424/59 |

FOREIGN PATENT DOCUMENTS

| | | |
|---|---|---|
| DE | 197 26 184 | 12/1998 |
| DE | 197 55 649 | 6/1999 |
| EP | 0 518 772 | 12/1992 |
| EP | 0 518 773 | 12/1992 |
| EP | 0 775 698 | 5/1997 |
| EP | 0 813 861 | 12/1997 |
| EP | 0 878 469 | 11/1998 |
| EP | 0 913 390 | 5/1999 |
| EP | 0 928 608 | 7/1999 |
| EP | 0 933 376 | 8/1999 |
| EP | 1 034 778 | 9/2000 |
| EP | 1 044 676 | 10/2000 |
| FR | 2 796 550 | 1/2001 |
| GB | 1539625 | 1/1979 |
| JP | 07277937 | 10/1995 |
| JP | 11189522 | 7/1999 |
| WO | WO 93/04665 | 3/1993 |
| WO | WO 98/25922 | 6/1998 |

*Primary Examiner*—Shelley A. Dodson
(74) *Attorney, Agent, or Firm*—Steptoe & Johnson LLP; D. Douglas Price

(57) ABSTRACT

A composition comprising at least one 1,3,5-triazine derivative and at least one N-acyl amino acid ester and its use in or for the manufacture of compositions, especially cosmetic and dermatological compositions for protecting the skin and/or the lips and/or integuments against ultraviolet radiation, in particular solar radiation. In addition, a cosmetic treatment process comprising the application of the cosmetic composition, and the use of the at least one N-acyl amino acid ester, in anti-sun compositions containing a 1,3,5-triazine derivative to improve the sun protection factor of the composition.

28 Claims, No Drawings

SOLUBILIZATION OF 1,3,5-TRIAZINE DERIVATIVES WITH N-ACYL AMINO ACID ESTERS

The present invention relates to a composition comprising at least one 1,3,5-triazine derivative and also to its use in or for the manufacture of cosmetic or dermatological compositions for protecting the skin and/or the lips and/or integuments against ultraviolet radiation, in particular solar radiation.

It is known that light radiation with wavelengths of between 280 nm and 400 nm permits tanning of the human epidermis, and that light rays with wavelengths of between 280 nm and 320 nm, known as UV-B rays, cause skin burns and erythema which may be harmful to the development of a natural tan; this UV-B radiation should thus be screened out.

It is also known that UV-A rays, with wavelengths of between 320 nm and 400 nm, which cause tanning of the skin, are liable to induce an adverse change in the latter, especially in the case of sensitive skin or of skin which is continually exposed to solar radiation. UV-A rays cause in particular a loss of elasticity of the skin and the appearance of wrinkles, leading to premature skin aging. They promote triggering of the erythemal reaction or amplify this reaction in certain individuals and may even be the cause of phototoxic or photoallergic reactions. It is thus desirable also to screen out UV-A radiation.

Many cosmetic compositions intended for the photoprotection (UV-A and/or UV-B) of the skin have been proposed to date.

These anti-sun compositions are quite often in the form of an emulsion of oil-in-water type (that is to say a cosmetically acceptable vehicle consisting of a continuous aqueous dispersing phase and a discontinuous. 1,3,5-Triazine derivatives are particularly desired in anti-sun cosmetics due to the fact that they are highly active in the UV-B range, and even in the UV-A range for some of these compounds, depending on the nature of the substituents involved. Furthermore, they are photostable, i.e., they show little or no chemical degradation under the action of UV radiation. They are especially described in U.S. Pat. No. 4,617,390, EP 863 145, EP 517 104, EP 570 838, EP 796 851, EP 775 698, EP 878 469 and EP 933 376, and the following are known in particular:

2,4,6-tris[p-(2'-ethylhexyl-1'-oxycarbonyl) anilino]-1,3,5-triazine or "Ethylhexyl Triazone" (INCI name), sold under the trade name "Uvinul T 150" by BASF, 2-[(p-(tert-butylamido)anilino]-4,6-bis-[(p-(2'ethylhexyl-1'-oxycarbonyl)anilino]-1,3,5-triazine or "Diethylhexyl Butamido Triazone" (INCI name), sold under the trade name "Uvasorb HEB" by Sigma 3V, and 2,4-bis{[4-2-ethylhexyloxy)]-2-hydroxy]phenyl}-6-(4-methoxyphenyl)-1,3,5-triazine or "Anisotriazine" (INCI name), sold under the trade name "Tinosorb S" by Ciba Specialty Chemicals.

It has been proposed in the prior art to use 1,3,5-triazine derivatives in oils such as esters and more particularly $C_{12}$–$C_{15}$ alkyl benzoates ("Finsolv TN" from Finetex), or triglycerides and especially $C_8$–$C_{12}$ fatty acid triglycerides ("Miglyol 812" from Hüls), or alternatively oxyethylenated or oxypropylenated fatty monoalcohols or polyols ("Cetiol HE" from Henkel or "Witconol AM" from Witco).

However, it has been observed that the photoprotective power of these triazine derivatives in the absence of other sunscreens is very limited and that their cosmetic properties are generally considered to be insufficient.

The problem posed underlying the present invention was that of improving the photoprotective efficacy of compositions containing such 1,3,5-triazine derivatives.

Surprisingly and unexpectedly, the inventors of the present patent application have shown that the use of at least one ester chosen from N-acyl amino acid esters of formula:

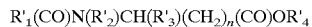

in which:

n is an integer equal to 0, 1 or 2, $R'_1$ represents a linear or branched $C_5$ to $C_{21}$ alkyl or alkenyl radical, $R'_2$ represents a hydrogen atom or a $C_1$ to $C_3$ alkyl group, $R'_3$ represents a radical chosen from the group formed by a hydrogen atom, a methyl group, an ethyl group and a linear or branched $C_3$ or $C_4$ alkyl chain, and radical or a sterol residue, makes it possible to obtain a composition containing 1,3,5-triazine derivatives that have improved cosmetic and photoprotective properties. These N-acyl amino acid esters, and also the process for preparing them, are described in EP 1 044 676 and EP 0 928 608 to Ajinomoto Co.

The main advantage of these N-acyl amino acid esters is that they allow the production of anti-sun compositions containing 1,3,5-triazine derivatives and have a sun protection factor that is greater than that of the compositions of the prior art containing 1,3,5-triazine derivatives.

These compositions also have improved cosmetic qualities. They allow good moisturization of the skin, i.e., no drying of the skin is observed, nor, on the contrary, any excessively greasy feel.

One subject of the present invention is thus a composition containing at least one 1,3,5-triazine derivative and at least one ester chosen from N-acyl amino acid esters.

Another subject of the invention consists in using such a composition to manufacture cosmetic or dermatological compositions.

A subject of the invention is also a cosmetic treatment process comprising the application of a composition according to the present invention, and also the use of at least one N-acyl amino acid ester of formula:

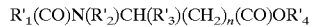

in which:

n is an integer equal to 0, 1 or 2, $R'_1$ represents a linear or branched $C_5$ to $C_{21}$ alkyl or alkenyl radical, $R'_2$ represents a hydrogen atom or a $C_1$ to $C_3$ alkyl group, $R'_3$ represents a radical chosen from the group formed by a hydrogen atom, a methyl group, an ethyl group and a linear or branched $C_3$ or $C_4$ alkyl chain, and $R'_4$ represents a linear or branched $C_1$ to $C_{10}$ alkyl radical or a linear or branched $C_2$ to $C_{10}$ alkenyl radical or a sterol residue, in anti-sun compositions containing a 1,3,5-triazine derivative, in order to improve the sun protection factor of this composition.

Other subjects of the invention will become apparent on reading the description and the examples that follow.

The composition that is the subject of the invention preferably comprises, in a physiologically acceptable medium:

(i) at least one 1,3,5-triazine derivative, and (ii) at least one ester chosen from N-acyl amino acid esters of formula:

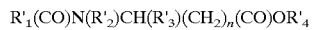

in which:

n is an integer equal to 0, 1 or 2, $R'_1$ represents a linear or branched $C_5$ to $C_{21}$ alkyl or alkenyl radical, $R'_2$ represents a hydrogen atom or a $C_1$ to $C_3$ alkyl group, $R'_3$ represents a radical chosen from the group formed by a hydrogen atom, a methyl group, an ethyl group and a linear or branched $C_3$ or $C_4$ alkyl chain, and $R'_4$ represents a linear or branched $C_1$ to $C_{10}$ alkyl radical or a linear or branched $C_2$ to $C_{10}$ alkyl radical or a sterol residue.

In the formula for the amino acid esters presented above, the group $R'_1(CO)$— is an acyl group of an acid preferably chosen from the group formed by capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These fatty acids may also contain a hydroxyl group. Even more preferably, the fatty acid is lauric acid.

The portion —$N(R'_2)CH(R'_3)(CH_2)_n(CO)$— of the amino acid ester is preferably chosen from the following amino acids: glycine, alanine, valine, leucine, isoleucine, serine, threonine, proline, hydroxyproline, β-alanine, aminobutyric acid, aminocaproic acid, sarcosine and N-methyl-β-alanine.

Even more preferably, the amino acid is sarcosine.

The portion of the amino acid esters corresponding to the group $OR'_4$ may be obtained from alcohols chosen from the group formed by methanol, ethanol, propanol, isopropanol, butanol, tert-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecyl alcohol and isostearyl alcohol.

These amino acid esters may be obtained in particular from natural sources of amino acids. In this case, the amino acids are obtained from the hydrolysis of natural proteins of plants (oat, wheat, soybean, palm or coconut) and then necessarily lead to mixtures of amino acids that will subsequently be esterified and then N-acylated. The preparation of such amino acids is more particularly described in FR 2 796 550, which is expressly incorporated herein by reference.

The amino acid ester that is more particularly preferred for use in the present invention is isopropyl N-lauroylsarcosinate of formula:

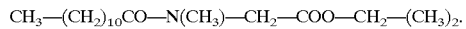

The 1,3,5-triazine derivative corresponds to formula (I) below:

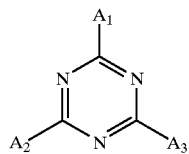

(i)

in which the radicals $A_1$, $A_2$ and $A_3$, which may be identical or different, are chosen from the group of formulas (II) to (IX) below:

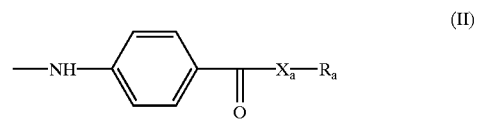

(II)

(III)

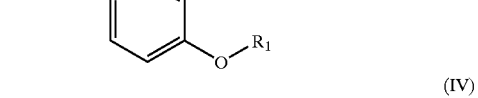

(IV)

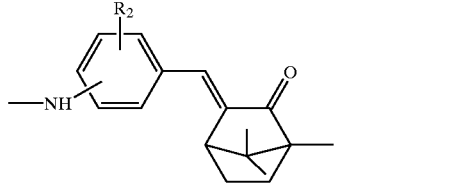

(V)

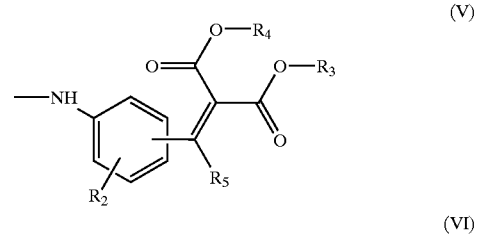

(VI)

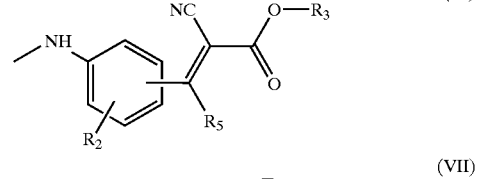

(VII)

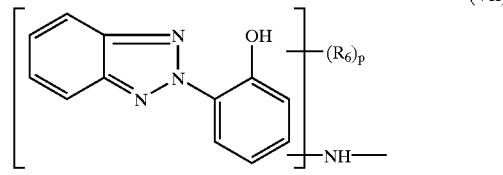

(VIII)

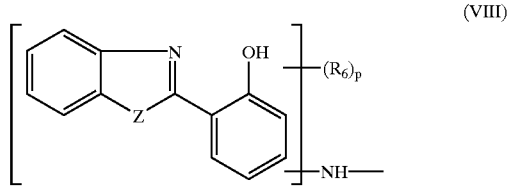

(IX)

in which:

$X_a$ (each of the groups $X_a$ may be identical or different) represents oxygen or —NH—;

$R_a$ (each of the groups $R_a$ may be identical or different) is chosen from hydrogen; an alkali metal; an ammonium radical optionally substituted with one or more linear or branched $C_1$–$C_{18}$ alkyl or linear or branched $C_1$–$C_{18}$ hydroxyalkyl radicals; a linear or branched $C_1$–$C_{18}$ and preferably $C_6$–$C_{12}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units, the terminal OH group of which is methylated; and a radical of formula (X), (XI) or (XII) below:

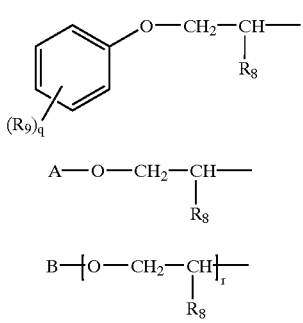

in which:
R$_8$ is hydrogen or a methyl radical;
R$_9$ is a C$_1$–C$_9$ alkyl radical;
q is an integer equal to 0; 1; 2; 3;
r is an integer equal to 1; 2; 3; 4; 5; 6; 7; 8; 9; 10;
A is a C$_4$–C$_8$ alkyl radical or a C$_5$–C$_8$ cycloalkyl radical;
B is chosen from: a linear or branched C$_1$–C$_8$ alkyl radical;
a C$_5$–C$_8$ cycloalkyl radical; and an aryl radical optionally substituted with one or more C$_1$–C$_4$ alkyl radicals; and
R$_1$ denotes a C$_3$–C$_{18}$ alkyl radical; a C$_2$–C$_{18}$ alkenyl radical; a residue of formula —CH$_2$—CH(OH)—CH$_2$—OT$_1$ in which T$_1$ is a hydrogen atom or a C$_1$–C$_8$ alkyl radical; or a residue of formula (XIII) below:

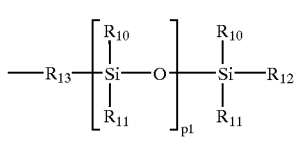

in which:
R$_{13}$ denotes a covalent bond; a linear or branched C$_1$–C$_4$ alkyl radical or a radical of formula —C$_{m1}$H$_{2m1}$— or —C$_{m1}$H$_{2m1}$—O— in which m$_1$ is an integer equal to 1; 2; 3; 4;
p$_1$ is an integer equal to 0; 1; 2; 3; 4; 5;
the radicals R$_{10}$, R$_{11}$ and R$_{12}$, which may be identical or different, denote a C$_1$–C$_{18}$ alkyl radical; a C$_1$–C$_{18}$ alkoxy radical or a radical of formula:

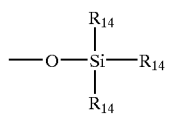

in which R$_{14}$ is a C$_1$–C$_5$ alkyl radical,
R$_2$ denotes a hydrogen atom, a linear or branched C$_{1-4}$ alkyl radical or a C$_1$–C$_4$ alkoxy radical;
R$_3$ and R$_4$, which may be identical or different, denote a linear or branched C$_1$–C$_{20}$ alkyl radical;
R$_5$ represents a hydrogen atom or a phenyl radical optionally substituted with a halogen or with a C$_1$–C$_4$ alkyl radical or with a C$_1$–C$_4$ alkoxy radical;
R$_6$ is a linear or branched C$_1$–C$_8$ alkyl radical or a C$_1$–C$_3$ alkoxy radical, it being understood that, in the latter case, two adjacent radicals R$_6$ on the same aromatic nucleus can together form an alkylidenedioxy group in which the alkylidene group contains 1 or 2 carbon atoms, OH, NHCOCH$_3$ or NH$_2$,
R$_7$ denotes a hydrogen atom, a C$_1$–C$_{10}$ alkyl radical, a radical of formula: —(CH$_2$CHR$_5$—O)$_{n1}$R$_8$ in which n1 is a number from 1 to 16, or a radical of structure —CH$_2$—CH—(OH)—CH$_2$OT$_1$ with R$_8$ and T$_1$ having the same meaning as indicated above,
Z represents oxygen, sulphur, —NH— or —NR$_3$— with R$_3$ representing a linear or branched C$_1$–C$_{20}$ alkyl radical;
p is 0, 1, 2 or 3, and
A$_1$ can also be a halogen, a radical —N(R$_3$)$_2$, the two radicals R$_3$ together possibly forming a ring of 4 or 5 carbon atoms, or a group —OR$_3$, R$_3$ having the same definition as above.

A first family of 1,3,5-triazine derivatives that is more particularly preferred, and that is described especially in EP-A-0 517 104, is that of the 1,3,5-triazines corresponding to formula (I) in which A$_1$, A$_2$ and A$_3$ are of formula (II) and have all of the following characteristics:
one of the groups X$_a$–R$_a$ represents a radical —NH—R$_a$ with R$_a$ chosen from: a C$_5$–C$_{12}$ cycloalkyl radical optionally substituted with one or more C$_1$–C$_4$ alkyl radicals; a radical of formula (X), (XI) or (XII) above in which:
B is a C$_1$–C$_4$ alkyl radical;
R$_9$ is a methyl radical;
the other two groups X$_a$–R$_a$ represent a radical —O—R$_a$ with R$_a$, which may be identical or different, chosen from: hydrogen;
an alkali metal; an ammonium radical optionally substituted with one or more alkyl or hydroxyalkyl radicals; a linear or branched C$_1$–C$_{18}$ alkyl radical; a C$_5$–C$_{12}$ cycloalkyl radical optionally substituted with one or more C$_1$–C$_4$ alkyl radicals; a radical of formula (X), (XI) or (XII) above in which:
B is a C$_1$–C$_4$ alkyl radical; and
R$_9$ is a methyl radical.

A second family of 1,3,5-triazine derivatives that is more particularly preferred, and that is described especially in EP-A-0 570 838, is that of the 1,3,5-triazines corresponding to formula (I) in which A$_1$, A$_2$ and A$_3$ are of formula (II) and have all of the following characteristics:
one or two groups X$_a$–R$_a$ represent a radical —NH—R$_a$, with R$_a$ chosen from: a linear or branched C$_1$–C$_{18}$ alkyl radical; a C$_5$–C$_{12}$ cycloalkyl radical optionally substituted with one or more C$_1$–C$_4$ alkyl radicals; a radical of formula (X), (XI) or (XII) above in which:
B is a C$_1$–C$_4$ alkyl radical; and
R$_9$ is a methyl radical;
the other or the other two group(s) X$_a$–R$_a$ being a radical —O—R$_a$ with R$_a$, which may be identical or different, chosen from: hydrogen; an alkali metal; an ammonium radical optionally substituted with one or more alkyl or hydroxyalkyl radicals; a linear or branched C$_1$–C$_{18}$ alkyl radical; a C$_5$–C$_{12}$ cycloalkyl radical optionally substituted with one or more C$_1$–C$_4$ alkyl radicals; and a radical of formula (X), (XI) or (XII) above in which:
B is a C$_1$–C$_4$ alkyl radical; and
R$_9$ is a methyl radical.

A 1,3,5-triazine of this second family that is particularly preferred is 2-[(p-(tert-butylamido)-anilino]-4,6-bis[(p-(2'-ethylhexyl-1'-oxycarbonyl)-anilino]-1,3,5-triazine or "Diethylhexyl Butamido Triazone" sold under the trade name "Uvasorb HEB" by Sigma 3V and corresponding to the following formula:

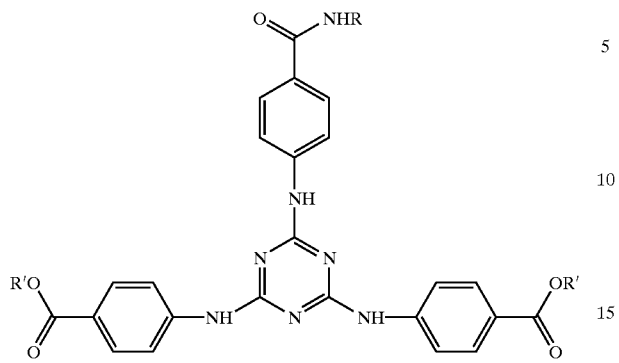

in which R' denotes a 2-ethylhexyl radical and R denotes a tert-butyl radical.

A third preferred family of compounds that may be used in the context of the present invention, and which is described especially in U.S. Pat. No. 4,724,137, is that of the 1,3,5-triazines corresponding to formula (I) in which $A_1$, $A_2$ and $A_3$ are of formula (II) and have all of the following characteristics:

$X_a$ are identical and represent oxygen; and
$R_a$, which may be identical or different, represent a $C_6$–$C_{12}$ alkyl radical or a polyoxyethylenated radical comprising from 1 to 6 ethylene oxide units and in which the terminal OH group is methylated.

A 1,3,5-triazine of this third family that is particularly preferred is 2,4,6-tris[p(2'-ethylhexyl-1'-oxycarbonyl)anilino]-1,3,5-triazine or "Ethylhexyl Triazone" sold especially under the trade name "Uvinul T 150" by BASF and which corresponds to the following formula:

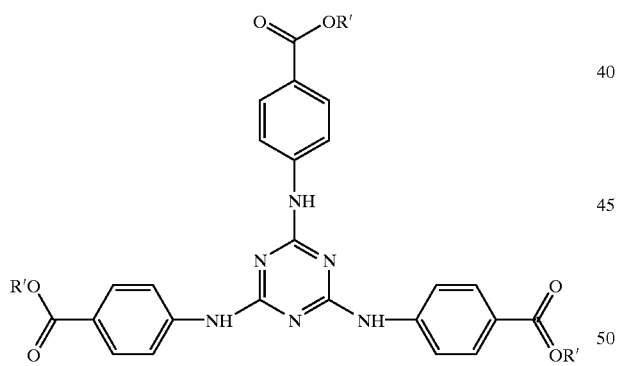

in which R' denotes a 2-ethylhexyl radical.

A fourth preferred family of compounds that may be used in the context of the present invention, and which is described especially in EP-A-0 775 698, is that of the 1,3,5-triazines corresponding to formula (I) in which $A_1$ and $A_2$ are of formula (III) and $A_3$ is of formula (IX) and have all of the following characteristics: $R_1$, which may be identical or different, denote a $C_3$–$C_{18}$ alkyl radical; a $C_2$–$C_{18}$ alkenyl radical or a residue of formula —$CH_2$—CH(OH)—$CH_2$—$OT_1$ in which $T_1$ is a hydrogen atom or a $C_1$–$C_8$ alkyl radical; and $R_7$ denotes a hydrogen atom or a $C_1$–$C_{10}$ alkyl radical.

A 1,3,5-triazine of this fourth family that is particularly preferred is 2,4-bis{[4-2-ethylhexyloxy)]-2-hydroxy]phenyl}-6-(4-methoxyphenyl)-1,3,5-triazine or "Anisotriaz-ine" sold under the trade name "Tinosorb S" by Ciba Specialty Chemicals, and corresponds to the following formula:

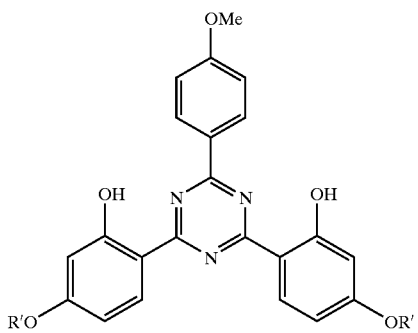

in which R' denotes a 2-ethylhexyl radical.

A fifth preferred family of compounds that may be used in the context of the present invention, and which is described especially in EP 507 691, EP 507 692, EP 790 243 and EP 944 624, and the technical content of which is expressly incorporated herein by reference, is that of the 1,3,5-triazines corresponding to formula (I) in which $A_1$, $A_2$ and $A_3$ are of formulae (VII) to (XI) mentioned above.

As examples of these compounds of the above formula that may be used, mention may be made of:

2,4,6-tris(diisobutyl 4'-aminobenzalmalonate)-s-triazine, 2,4,6-tris(bis(2-ethylhexyl)4'-aminobenzalmalonate)-s-triazine, 2,4,6-tris(bis(2-ethylhexyl)4'-aminobenzalmalonate)-6-chloro-s-triazine, 2,4,6-tris(bis(2-ethylhexyl)4'-aminobenzalmalonate)-6-(2-ethylhexyl4'-aminobenzoate)-s-triazine, 2,4,6-tris(diisobutyl4'-aminobenzalmalonate)-6-butoxy-s-triazine, 2,4,6-tris(diisobutyl4'-aminobenzalmalonate)-6-(2-ethylhexylamino)-s-triazine, 2,4-bis(4'-aminobenzylidenecamphor)-6-(2-ethylhexylamino)-s-triazine, 2,4-bis(4'-aminobenzylidenecamphor)-6-(diisobutyl4'-aminobenzalmalonate)-s-triazine, 2,4,6-tris(diethyl 4'-aminobenzalmalonate)-s-triazine, 2,4,6-tris(diisopropyl4'-aminobenzalmalonate)-s-triazine, 2,4,6-tris(dimethyl 4'-aminobenzalmalonate)-s-triazine, 2,4,6-tris(ethylα-cyano-4-aminocinnamate)-s-triazine, 2,4,6-tris[(3'-benzotriazol-2-yl-2'-hydroxy-5'-methyl)phenylamino]-s-triazine, and 2,4,6-tris[(3'-benzotriazol-2-yl-2'-hydroxy-5'-tert-octyl)phenylamino]-s-triazine.

A 1,3,5-triazine of this fifth family that is particularly preferred is 2,4,6-tris(diisobutyl 4'-aminobenzalmalonate)-s-triazine, which corresponds to the following formula:

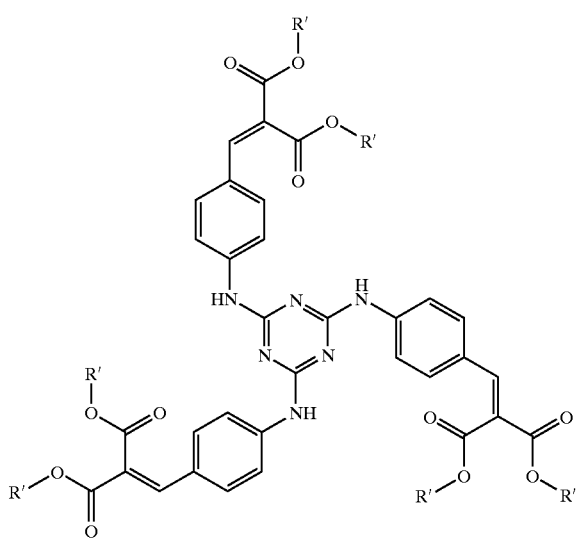

The compositions according to the present invention preferably comprise, in a physiologically acceptable medium, from 0.05% to 15%, and preferably from 0.1% to 10%, of 1,3,5-triazine derivatives by weight relative to the total weight of the composition.

The compositions according to the present invention preferably comprise, in a physiologically acceptable medium, from 0.1% to 50%, and preferably from 1% to 30%, of N-acyl amino acid esters by weight relative to the total weight of the composition.

The composition according to the present invention is preferably a cosmetic composition containing, besides the 1,3,5-triazine derivative as organic screening agent, at least one other additional UV-A-active and/or UV-B-active organic screening agent (absorber) that is water-soluble, liposoluble or insoluble in the cosmetic solvents commonly used.

These organic UV screening agents are chosen from dibenzoylmethane derivatives, cinnamic derivatives, anthranilates; salicylic derivatives; camphor derivatives; benzophenone derivatives; β, β-diphenylacrylate derivatives; benzotriazole derivatives; benzalmalonate derivatives; benzimidazole derivatives; imidazolines; bis-benzazolyl derivatives as described in EP 669 323 and U.S. Pat. No. 2,463,264; p-aminobenzoic acid (PABA) derivatives; methylenebis(hydroxyphenyl)benzotriazole derivatives as described in U.S. Pat. Nos. 5,237,071 and 5,166,355, GB 2 303 549, DE 197 26 184 and EP 893 119; screening polymers and screening silicones such as those described especially in WO 93/04665; dimers derived from α-alkylstyrene, such as those described in DE 198 55 649, 4,4-diarylbutadienes such as those described in EP 0 967 200 and DE 197 55 649 (the disclosures of which are expressly incorporated herein by reference).

The para-benzoic acid derivatives that may be used in the compositions according to the present invention are as follows, and their INCI names are added in parentheses:
  p-aminobenzoic acid (PABA),
  2-ethyl-p-aminobenzoic acid (ethyl PABA)
  (ethyl dihydroxypropyl PABA) sold under the name Amerscreen-P by Amerchol,
  2-ethylhexyl p-dimethylaminobenzoate (ethylhexyl dimethyl PABA) sold especially under the trade name "Escalol 507" by ISP,
  glyceryl p-aminobenzoate (glyceryl PABA),
  ethoxylated (25 mol) p-aminobenzoate (PEG-25 PABA) sold under the trade name "Uvinul P25" by BASF, and
  N-propoxylated ethyl p-aminobenzoate.

The salicylic derivatives that may be used in the compositions according to the present invention are as follows, and their INCI names are added in parentheses:
  homomenthyl salicylate (homosalate) sold under the trade name "Eusolex HMS" by Rona/EM Industries,
  2-ethylhexyl salicylate (ethylhexyl salicylate) sold under the trade name "Neo Heliopan OS" by Haarmann and Reimer,
  (dipropylene glycol salicylate) sold under the trade name "Dipsal" by Scher,
  triethanolamine salicylate (TEA salicylate) sold under the trade name "Neo Heliopan TS" by Haarmann and Reimer, and
  4-isopropylbenzyl salicylate.

The dibenzoylmethane derivatives that may be used in the compositions according to the present invention are as follows:
  2-methyldibenzoylmethane,
  4-methyldibenzoylmethane,
  4-isopropyldibenzoylmethane,
  4-tertbutyldibenzoylmethane,
  2,4-dimethyldibenzoylmethane,
  2,5-dimethyldibenzoylmethane,
  4,4-diisopropyldibenzoylmethane,
  4,4-dimethoxydibenzoylmethane,
  4-tert-butyl-4'-methoxydibenzoylmethane,
  2-methyl-5-isopropyl-4'-methoxydibenzoylmethane,
  2-methyl-5-tert-butyl-4'-methoxydibenzoylmethane,
  2,4-dimethyl-4'-methoxydibenzoylmethane, and
  2,6-dimethyl-4-tert-butyl-4'-methoxydibenzoylmethane.

Among the dibenzoylmethane derivatives mentioned above, the one that is particularly preferred is 4-tert-butyl-4'-methoxydibenzoylmethane (butyl methoxydibenzoylmethane), sold especially under the trade name "Parsol® 1789" by Hoffmann-Laroche.

Another dibenzoylmethane derivative that is preferred according to the present invention is 4-isopropyldibenzoylmethane (isopropyl dibenzoylmethane) sold under the name "Eusolex® 8020" by Merck.

The cinnamic derivatives that may be used in the compositions according to the present invention are as follows:
  2-ethylhexyl 4-methoxycinnamate (ethylhexyl methoxycinnamate) sold under the trade name "Parsol MCX" by Hoffmann La Roche,
  isopropyl methoxycinnamate,
  isoamyl 4-methoxycinnamate (isoamyl methoxy cinnamate) sold under the trade name "Neo Heliopan E 1000" by Haarmann and Reimer,
  cinoxate,
  diethanolamine 4-methoxycinnamate (DEA methoxycinnamate),
  methyl diisopropylcinnamate (diisopropyl methylcinnamate), and
  (glyceryl ethylhexanoate dimethoxycinnamate).

The β, β'-diphenylacrylate derivatives that may be used in the compositions according to the present invention are as follows:

2-ethylhexyl 2-cyano-3,3-diphenylacrylate (octocrylene) sold under the trade name "Uvinul N539" by BASF, and 2-ciano-3,3-diphenylacrylate (ethocrylene) sold under the trade name "Uvinul N35" by BASF.

The benzophenonederivatesthat may be used in the compositions according to the present invention are as follows:

2,4-dihydroxybenzophenone (benzophenone-1), this product being sold under the name Uvinul® 400 by BASF;

2,2',4,4'-tetrahydroxbenzophenone (benzophenone-2), this product being sold under the name Uvinul® D50 by BASF;

2-hydroxy-4-methoxybenzophenone, also known as oxybenzone (benzophenone-3), this procduct being sold under the name Uvinul® M40 by BASF;

2-hydroxy-4-methoxybenzophenone-5-sulphonic acid, also known as sulisobenzone (benzophenone-4), this product being sold under the name Uvinul® MS 40 by BASF; and also the sodium sulphonate form thereof (benzophenone-5);

2,2'-dihydroxy-4,4'-dimethoxybenzophenone (benzophenone-6), this product being sold under the name Heliosorb® 11 by Norquay;

5-chloro-2-hydroxybenone (benzophenone-13);

2,2'-dihydroxy-4-methoxybenzophenone, also known as dioxybenzone or benzophenone-8, this product being sold under the name Spectra-Sorb® UV-24 by American Cyanamid;

the disodium salt of 2,2'-dihydroxy-4,4'-dimethoxybenzophenone-5,5'-disulphonic acid (benzophenone-9), this product being sold under the name Uvinul® DS49 by BASF;

2-hydroxy-4-methoxy-4'-methylbenzophenone (benzophenone-7); and 2-hydroxy-4-(octyloxy)benzophenone (benzophenone-12).

The benzylidenecamphor derivatives that may be used in the compositions according to the present invention are as follows:

3-benzylidene-d,1-camphor (3-benzylidene camphor) manufactured under the trade name "Mexoryl SD" by Chimex, 3-(4'-methylbenzylidene)-d,1-camphor (4-methylbenzylidene camphor) sold under the trade name "Eusolex 6300" by Merck, (benzylidene camphor sulfonic acid) manufactured under the trade name "Mexoryl SL" by Chimex, (camphor benzalkonium methosulfate) manufactured under the trade name "Mexoryl SO" by Chimex, (terephtalylidene dicamphor sulfonic acid) manufactured under the trade name "Mexoryl SX" by Chimex, (polyacrylamidomethyl benzylidene camphor) manufactured under the trade name "Mexoryl SW" by Chimex.

The benzimidazole derivatives that may be used in the compositions according to the present invention are as follows:

2-phenylbenzimidazolyl-5-sulphonic acid sold under the trade name "Eusolex 232" by Merck, benzimidazilate sold under the trade name "Neo Heliopan AP" by Haarmann and Reimer.

The benzotriazole derivatives that may be used in the compositions according to the present invention are as follows:

drometrizole trisiloxane sold under the name "Silatrizole" by Rhodia Chimie, and methylenebis(benzotriazolyl)tetramethylbutylphenol, sold in solid form under the trade name "Mixxim BB/100" by Fairmount Chemical, or in micronized form as an aqueous dispersion under the trade name "Tinosorb M" by Ciba Specialty Chemicals.

Among the anthranilates that may be used according to the present invention, mention may be made most particularly of menthyl anthranilate, sold under the trade name "Neo Heliopan MA®" by Haarmann and Reimer.

Among the imidazoline derivatives that may be used according to the present invention, mention may be made most particularly of ethylhexyl dimethoxybenzylidene dioxoimidazoline propionate.

Among the benzalmalonate derivatives that may be used according to the present invention, mention may be made of polyorganosiloxanes containing a benzalmalonate function, such as the product sold under the trade name "Parsol SLX" by Hoffmann Laroche.

The organic UV screening agents that are preferred for the purposes of the present invention are chosen from the following compounds:

ethylhexyl salicylate, octocrylene, phenylbenzimidazole sulfonic acid, 4-methylbenzylidene camphor, benzimidazilate, terephthalylidene dicamphor sulfonic, benzophenone-3, benzophenone-4, benzophenone-5, methylene bis-benzotriazolyl tetramethylbutylphenol, drometrizole trisiloxane and mixtures thereof.

The composition may also comprise nacres, pigments or nanopigments (average size of the primary particles: generally between 5 nm and 100 nm and preferably between 10 nm and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, and mixtures thereof, which are all UV photoprotective agents that are well known per se. Standard coating agents are, moreover, alumina and/or aluminium stearate. Such coated or uncoated metal oxide nanopigments are described in particular in EP-A-0 518 772 and EP-A-0 518 773.

The compositions of the invention may also comprise standard cosmetic adjuvants chosen especially from fatty substances, organic solvents other than those used specifically in the context of the present invention, emulsifiers, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preserving agents, surfactants, anti-inflammatories, substance P antagonists, fillers, polymers, propellants, acidifying or basifying agents, colorants or any other ingredient usually used in cosmetics, in particular for the manufacture of anti-sun compositions in the form of emulsions.

The fatty substances may consist of an oil or a wax or mixtures thereof, and they also comprise fatty acids, fatty alcohols and fatty acid esters. The oils may be chosen from animal, plant, mineral and synthetic oils, and especially from liquid petroleum jelly, liquid paraffin, volatile or nonvolatile silicone oils, isoparaffins, polyolefins, fluoro oils, perfluoro oils, and alkyl derivatives of benzoic acid and of hydrobenzoic acid. Similarly, the waxes may be chosen from animal, fossil, plant, mineral and synthetic waxes that are known per se.

Among the organic solvents that may be mentioned are lower alcohols and polyols.

Needless to say, a person skilled in the art will take care to select this or these optional additional compound(s) and/or the amounts thereof such that the advantageous properties, in particular the increase of the protection factor of the 1,3,5-triazine derivatives in the N-acyl amino acid ester, are not, or are not substantially, adversely affected by the envisaged addition(s).

The compositions of the invention may be prepared according to techniques that are well known to those skilled in the art, in particular those intended for preparing emulsions of oil-in-water (O/W) or water-in-oil (W/O) type.

These compositions may be in particular in the form of a simple emulsion or a complex emulsion: double (O/W or W/O) or triple (W/O/W or O/W/O) emulsion, such as a cream, a milk, a gel or a cream-gel; a powder or a solid tube, and may optionally be packaged as an aerosol and may be in the form of a mousse or spray.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The cosmetic composition of the invention may be used as a composition for protecting the human epidermis or the hair against ultraviolet rays, as an anti-sun composition or as a makeup product.

When the cosmetic composition according to the invention is used for protecting the human epidermis against UV rays, or as an anti-sun composition, it may be in the form of a suspension or a dispersion in solvents or fatty substances, in the form of a nonionic vesicular dispersion or in the form of an emulsion, preferably of oil-in-water type, such as a milk or a cream, or in the form of an ointment, a gel, a cream-gel, a solid tube, a powder, a stick, an aerosol mousse or a spray.

When the cosmetic composition according to the invention is used for protecting the hair against UV rays, it may be in the form of a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or straightening the hair, a styling or treating lotion or gel, a blow-drying or hairsetting lotion or gel, or a permanent-waving, straightening, dyeing or bleaching composition for the hair.

When the composition is used as a makeup product for the nails, the eyelashes, the eyebrows or the skin, such as an epidermal treatment cream, a foundation, a tube of lipstick, an eyeshadow, a face powder, mascara or an eyeliner, it may be in solid, pasty, anhydrous or aqueous form, for instance oil-in-water or water-in-oil emulsions, nonionic vesicular dispersions or suspensions.

As a guide, for the anti-sun formulations in accordance with the invention that contain a support of oil-in-water emulsion type, the aqueous phase (especially comprising the hydrophilic screening agents) generally represents from 50% to 95% by weight, and preferably from 70% to 90% by weight, relative to the total weight of the formulation, the oily phase (especially comprising the lipophilic screening agents) from 5% to 50% by weight, and preferably from 10% to 30% by weight, relative to the total weight of the formulation, and the (co)emulsifier(s) from 0.5% to 20% by weight, and preferably from 2% to 10% by weight, relative to the total weight of the formulation.

The present invention also relates to the use of a composition according to the present invention in or for the manufacture of cosmetic or dermatological compositions for protecting the skin and/or the lips and/or integuments (eyelashes, eyebrows, hair and nails) against ultraviolet radiation, in particular solar radiation, and also to a cosmetic treatment process, characterized in that it consists in applying a composition according to the present invention to the skin, the lips or integuments.

The example that follows illustrates the invention without limiting its scope.

EXAMPLE

Two antisun compositions (C1 in accordance with the invention and comparative C2) were prepared in the form of emulsions of oil-in-water type.

| Composition | C1 | C2 |
|---|---|---|
| 80/20 mixture of cetylstearyl alcohol and of oxyethylenated (33 EO) cetylstearyl alcohol (Sinnowax AO - Henkel) | 7 | 7 |
| Mixture of glyceryl mono- and distearate (Cerasynt SD-V ISP) | 2 | 2 |
| Cetyl alcohol | 1.5 | 1.5 |
| Polydimethylsiloxane (Dow Corning 200 Fluid - Dow Corning) | 1.5 | 1.5 |
| C12/C15 alkylbenzoates (Witconol TN - Witco) | | 15 |
| Isopropyl lauroyl sarcosinate (Eldew SL, 205 - Ajinomoto) | 15 | |
| Uvinul T150 | 10 | 10 |
| Glycerol | 20 | 20 |
| Preserving agents | qs | qs |
| Demineralized water qs | 100 g | 100 g |

For each of the formulations thus prepared, the sun protection factor (SPF) associated therewith was then determined. This was determined using the in vitro method described by B. L. Diffey et al. in J. Soc. Cosmet. Chem. 40-127–133 (1989), this method consisting in determining the monochromatic protection factors every 5 nm in a wavelength range from 290 to 400 nm and calculating therefrom the sun protection factor according to a given mathematical equation.

The results obtained were as follows:

| Formulations | Oil | In vitro SPF |
|---|---|---|
| C1 | N-acyl amino acid ester | 10.1 + 0.4 |
| C2 comparative | Miglyol 212 | 7.9 + 0.7 |

These results clearly show the improvement in the sun protection factor of the composition according to the invention due to the presence of an N-acyl amino acid ester.

What is claimed is:

1. A composition, comprising:
(i) at least one 1,3,5-triazine derivative, and
(ii) at least one N-acyl amino acid ester of formula:

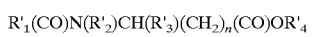

in which:
n is a 0, 1 or 2 integer,
R'$_1$ represents a linear or branched $C_5$ to $C_{21}$ alkyl or alkenyl radical,
R'$_2$ represents a hydrogen atom or a $C_1$ to $C_3$ alkyl group,
R'$_3$ represents a hydrogen atom, a methyl group, an ethyl group or a linear or branched $C_3$ or $C_4$ alkyl chain, and
R'$_4$ represents a linear or branched $C_1$ to $C_{10}$ alkyl radical, a linear or branched $C_2$ to $C_{10}$ alkenyl radical or a sterol residue.

2. The composition according to claim 1, wherein the 1,3,5-triazine derivative is a derivative of formula (I):

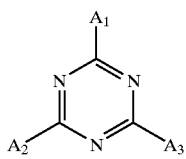
(I)

in which the radicals $A_1$, $A_2$ and $A_3$, which may be identical or different, have one of the formulas (II) to (IX):

(II)

(III)

(IV)

(V)

(VI)

(VII)

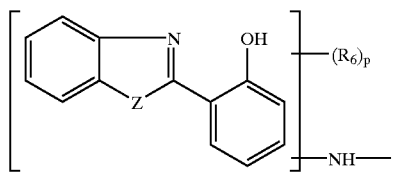
(VIII)

(IX)

in which:
$X_a$ represents oxygen or —NH—, and
$R_a$ is a hydrogen atom, an alkali metal, an ammonium radical optionally substituted with one or more linear or branched $C_1$–$C_{18}$ alkyl, or linear or branched $C_1$–$C_{18}$ hydroxyalkyl, radicals, a linear or branched $C_1$–$C_{18}$ radical, a $C_5$–$C_{12}$ cycloalkyl radical optionally substituted with one or more $C_1$–$C_4$ alkyl radicals, a polyoxyethylenated radical comprising from 1 to 6 ethylene oxide units, the terminal OH group of which is methylated, or a radical of formula (X), (XI) or (XII):

(X)

(XI)

(XII)

in which:
$R_8$ is a hydrogen atom or a methyl radical,
$R_9$ is a $C_1$–$C_9$ alkyl radical,
q is a 0, 1, 2, or 3 integer,
r is a 1, 2, 3, 4, 5, 6, 7, 8, 9, or 10 integer,
A is a $C_4$–$C_8$ alkyl radical or a $C_5$–$C_8$ cycloalkyl radical,
B is a linear or branched $C_1$–$C_8$ alkyl radical, a $C_5$–$C_8$ cycloalkyl radical, or an aryl radical optionally substituted with one or more $C_1$–$C_4$ alkyl radicals, and
$R_1$ denotes a $C_3$–$C_{18}$ alkyl radical, a $C_2$–$C_{18}$ alkenyl radical, a residue of formula —CH$_2$—CH(OH)—CH$_2$—OT$_1$ in which $T_1$ is a hydrogen atom or a $C_1$–$C_8$ alkyl radical, or a residue of formula (XIII):

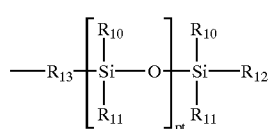
(XIII)

in which:
$R_{13}$ denotes a covalent bond, a linear or branched $C_1$–$C_4$ alkyl radical or a radical of formula —$C_{m1}H_{2m1}$— or —$C_{m1}H_{2m1}$—O— in which $m_1$ is a 1, 2, 3, or 4 integer,
$p_1$ is a 0, 1, 2, 3, 4, or 5 integer, and $R_{10}$, $R_{11}$ and $R_{12}$, which may be identical or different, denote a $C_1$–$C_{18}$ alkyl radical, a $C_1$–$C_{18}$ alkoxy radical or a radical of formula (XIV):

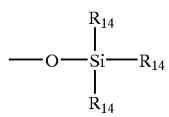
(XIV)

in which $R_{14}$ is a $C_1$–$C_5$ alkyl radical, $R_2$ denotes a hydrogen atom, a linear or branched $C_{1-4}$ alkyl radical or a $C_1$–$C_4$ alkoxy radical, $R_3$ and $R_4$, which may be identical or different, denote a linear or branched $C_1$–$C_{20}$ alkyl radical, $R_5$ represents a hydrogen atom or a phenyl radical optionally substituted with a halogen or with a $C_1$–$C_4$ alkyl radical or with a $C_1$–$C_4$ alkoxy radical, $R_6$ is a linear or branched $C_1$–$C_8$ alkyl radical or a $C_1$–$C_3$ alkoxy radical, it being understood that, when $R_6$ is a $C_1$–$C_3$ alkoxy radical, two adjacent radicals $R_6$ on the same aromatic nucleus may together form an alkylidenedioxy group in which the alkylidene group contains 1 or 2 carbon atoms, OH, NHCOCH$_3$ or NH$_2$, $R_7$ denotes a hydrogen atom, a $C_1$–$C_{10}$ alkyl radical, a radical of formula: —(CH$_2$CHR$_5$—O)$_{n1}$R$_8$ in which n1 is a number from 1 to 16, or a radical of structure —CH$_2$—CH—(OH)—CH$_2$OT$_1$ with $R_8$ and $T_1$ having the same meaning as stated above, Z represents oxygen, sulphur, —NH— or —NR$_3$— with $R_3$ representing a linear or branched $C_1$–$C_{20}$ alkyl radical, p is 0, 1, 2 or 3, and wherein $A_1$ may also be a halogen atom, a radical —N(R$_3$)$_2$, the two radicals $R_3$ together optionally forming a ring of 4 or 5 carbon atoms, or a group —OR$_3$, $R_3$ having the same meaning as above.

3. The composition according to claim 2, wherein the 1,3,5-triazine derivative is a derivative of formula (I) in which $A_1$, $A_2$ and $A_3$ are of formula (II) and have all of the following characteristics:

one of the groups $X_a$–$R_a$ represents a radical —NH—$R_a$ with $R_a$ is a $C_5$–$C_{12}$ cycloalkyl radical optionally substituted with one or more $C_1$–$C_4$ alkyl radicals or a radical of formula (X), (XI) or (XII) above in which:
B is a $C_1$–$C_4$ alkyl radical,
$R_9$ is a methyl radical,
the other two groups $X_a$–$R_a$ represent a radical —O—$R_a$ wherein $R_a$, which may be identical or different, is a hydrogen atom, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, or a radical of formula (X), (XI) or (XII) above in which:
B is a $C_1$–$C_4$ alkyl radical, and
$R_9$ is a methyl radical.

4. The composition according to claim 2, wherein the 1,3,5-triazine corresponds to formula (I) in which $A_1$, $A_2$ and $A_3$ are of formula (II) and have all of the following characteristics:

one or two groups $X_a$–$R_a$ represent a radical —NH—$R_a$, wherein $R_a$ is a linear or branched $C_1$–$C_{18}$ alkyl radical, a $C_5$–$C_{12}$ cycloalkyl radical optionally substituted with one or more $C_1$–$C_4$ alkyl radicals, or a radical of formula (X), (XI) or (XII) above in which:
B is a $C_1$–$C_4$ alkyl radical, and
$R_9$ is a methyl radical,
the other or the other two groups $X_a$–$R_a$ being a radical —O—$R_a$ wherein $R_a$, which may be identical or different, is a hydrogen atom, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, or a radical of formula (X), (XI) or (XII) above in which:
B is a $C_1$–$C_4$ alkyl radical, and
$R_9$ is a methyl radical.

5. The composition according to claim 4, wherein the 1,3,5-triazine is 2-[(p-(tert-butylamido)anilino]-4,6-bis[(p-(2'-ethylhexyl-1'-oxycarbonyl)anilino]-1,3,5-triazine.

6. The composition according to claim 2, wherein the 1,3,5-triazine corresponds to formula (I) in which $A_1$, $A_2$ and $A_3$ are of formula (II) and have all of the following characteristics:

$X_a$ are identical and represent oxygen, and $R_a$, which may be identical or different, represents a $C_6$–$C_{12}$ alkyl radical or a polyoxyethylenated radical comprising from 1 to 6 ethylene oxide units and in which the terminal OH group is methylated.

7. The composition according to claim 6, wherein the 1,3,5-triazine is 2,4,6-tris[p-(2'-ethylhexyl-1'-oxycarbonyl)anilino]-1,3,5-triazine.

8. The composition according to claim 2, wherein the 1,3,5-triazine corresponds to formula (I) in which $A_1$ and $A_2$ are of formula (III) and $A_3$ is of formula (IX) and have all of the following characteristics:

$R_1$, which may be identical or different, denotes a $C_3$–$C_{18}$ alkyl radical, a $C_2$–$C_{18}$ alkenyl radical or a residue of formula CH$_2$—CH(OH)—CH$_2$—OT$_1$ in which $T_1$ is a hydrogen atom or a $C_1$–$C_8$ alkyl radical, and $R_7$ denotes a hydrogen atom or a $C_1$–$C_{10}$ alkyl radical.

9. The composition according to claim 8, wherein the 1,3,5-triazine is 2,4-bis{[4-2-ethylhexyloxy)]-2-hydroxy]phenyl}-6-(4-methoxyphenyl)-1,3,5-triazine.

10. The composition according to claim 2, wherein the 1,3,5-triazine corresponds to formula (I) in which $A_1$, $A_2$ and $A_3$ are of formulae (VII) to (XI).

11. The composition according to claim 10, wherein the 1,3,5-triazine is:

2,4,6-tris(diisobutyl 4'-aminobenzalmalonate)-s-triazine, 2,4,6-tris(bis(2-ethylhexyl) 4'-aminobenzalmalonate)-s-triazine, 2,4,6-tris(bis(2-ethylhexyl) 4'-aminobenzalmalonate)-6-chloro-s-triazine, 2,4,6-tris(bis(2-ethylhexyl) 4'-aminobenzalmalonate)-6-(2-ethylhexyl 4'-aminobenzoate)-s-triazine, 2,4,6-tris(diisobutyl 4'-aminobenzalmalonate)-6-butoxy-s-triazine, 2,4,6-tris(diisobutyl 4'-aminobenzalmalonate)-6-(2-ethylhexylamino)-s-triazine, 2,4-bis(4'-aminobenzylidenecamphor)-6-(2-ethylhexylamino)-s-triazine, 2,4-bis(4'-aminobenzylidenecamphor)-6-(diisobutyl 4'-aminobenzalmalonate)-s-triazine, 2,4,6-tris(diethyl 4'-aminobenzalmalonate)-s-triazine, 2,4,6-tris(diisopropyl 4'-aminobenzalmalonate)-s-triazine, 2,4,6-tris(dimethyl 4'-aminobenzalmalonate)-s-triazine, 2,4,6-tris(ethyl α-cyano-4-aminocinnamate)-s-triazine, 2,4,6-tris[(3'-benzotriazol-2-yl-2'-hydroxy-5'-methyl)phenylamino]-s-triazine, or 2,4,6-tris[(3'-benzotriazol-2-yl-2'-hydroxy-5'-tert-octyl)phenylamino]-s-triazine.

12. The composition according to claim 1, wherein the amino acid ester is isopropyl N-lauroylsarcosinate having the formula:

$$CH_3-(CH_2)_{10}CO-N(CH_3)-CH_2-COO-CH_2-(CH_3)_2.$$

13. The composition according to claim 1, wherein the composition comprises, in a physiologically acceptable medium, from 0.05% to 15% of 1,3,5-triazine derivative by weight relative to the total weight of the composition.

14. The composition according to claim 1, wherein the composition comprises, in a physiologically acceptable medium, from 0.1% to 10% of 1,3,5-triazine derivative by weight relative to the total weight of the composition.

15. The composition according to claim 1, wherein the composition comprises, in a physiologically acceptable medium, from 0.1% to 50% of N-acyl amino acid ester derivative by weight relative to the total weight of the composition.

16. The composition according to claim 1, wherein the composition comprises, in a physiologically acceptable medium, from 1% to 30% of N-acyl amino acid ester derivative by weight relative to the total weight of the composition.

17. The composition according to claim 1, wherein the composition is a cosmetic composition that contains, in addition to the 1,3,5-triazine derivative, at least one other additional UV-A-active and/or UV-B-active organic screening agent.

18. The composition according to claim 17, wherein the organic UV screening agent is a dibenzoylmethane derivative, a cinnamic derivative, an anthranilate, a salicylic derivative, a camphor derivative, a benzophenone derivative, a β,β-diphenylacrylate derivative, a benzotriazole derivative, a benzalmalonate derivative, a benzimidazole derivative, an imidazoline, a bis-benzazolyl derivative, a p-aminobenzoic acid (PABA) derivative, a methylenebis(hydroxyphenyl)benzotriazole derivative, a screening polymer and screening silicone, a dimer derived from α-alkylstyrene and a 4,4-diarylbutadiene.

19. The composition according to claim 18, wherein the organic UV screening agent is:

ethylhexyl salicylate, octocrylene, phenylbenzimidazole sulfonic acid, 4-methylbenzylidene camphor, benzimidazilate, terephthalylidene dicamphor sulfonic, benzophenone-3, benzophenone-4, benzophenone-5, methylene bis-benzotriazolyl tetramethylbutylphenol, drometrizole trisiloxane or mixtures thereof.

20. The composition according to claim 1, wherein the composition also comprises nacres and coated or uncoated metal oxide pigments or nanopigments.

21. The composition according to claim 20, wherein the pigments or nanopigments are titanium oxide, zinc oxide, iron oxide, zirconium oxide, cerium oxide, or mixtures thereof.

22. The composition according to claim 1, wherein the composition also comprises at least one adjuvant which is a fatty substance, an organic solvent, an emulsifier, an ionic or nonionic thickener, a softener, an antioxidant, a free-radical scavenger, an opacifier, a stabilizer, an emollient, a silicone, an α-hydroxy acid, an antifoam, a moisturizer, a vitamin, an insect repellent, a fragrance, a preserving agent, a surfactant, an anti-inflammatory, a substance P antagonist, a filler, a polymer, a propellant, an acidifying or basifying agent, or a colorant.

23. The composition according to claim 1, wherein the composition is a composition for protecting the human epidermis or an anti-sun composition and wherein the composition is in the form of a nonionic vesicular dispersion, an emulsion, a cream, a triple emulsion (W/O/W or O/W/O), a milk, a gel, a cream-gel, a suspension, a dispersion, a powder, a solid tube, a mousse or a spray.

24. The composition according to claim 1, wherein the composition is a makeup composition for eyelashes, eyebrows or skin and wherein the composition is in solid, pasty, anhydrous or aqueous form or in the form of an emulsion, a suspension or a dispersion.

25. The composition according to claim 1, wherein the composition is a composition for protecting the hair against ultraviolet rays and wherein the composition is in the form of a shampoo, a lotion, a gel, an emulsion or a nonionic vesicular dispersion.

26. A process for using the composition according to claim 1, comprising using the composition in or for the manufacture of cosmetic or dermatological compositions for protecting the skin and/or the lips and/or integuments against ultraviolet radiation, in particular solar radiation.

27. A cosmetic treatment process, comprising applying a composition according to claim 1 to the skin and/or the lips and/or integuments.

28. A process of using at least one N-acyl amino acid ester of formula:

$$R'_1(CO)N(R'_2)CH(R'_3)(CH_2)_n(CO)OR'_4$$

in which:

n is a 0, 1 or 2 integer, $R'_1$ represents a linear or branched $C_5$ to $C_{21}$ alkyl or alkenyl radical, $R'_2$ represents a hydrogen atom or a $C_1$ to $C_3$ alkyl group, $R'_3$ represents a hydrogen atom, a methyl group, an ethyl group or a linear or branched $C_3$ or $C_4$ alkyl chain, $R'_4$ represents a linear or branched $C_1$ to $C_{10}$ alkyl radical, a linear or branched $C_2$ to $C_{10}$ alkenyl radical or a sterol residue, comprising adding the at least one N-acyl amino acid ester to an anti-sun composition containing a 1,3,5-triazine derivative in order to improve the sun protection factor of the composition.

* * * * *